United States Patent [19]

Crawford et al.

[11] Patent Number: 5,200,338

[45] Date of Patent: Apr. 6, 1993

[54] BACTERIAL EXTRACELLULAR LIGNIN PEROXIDASE

[75] Inventors: Donald L. Crawford; Muralidhara Ramachandra, both of Moscow, Id.

[73] Assignee: Idaho Research Foundation, Incorporation, Moscow, Id.

[21] Appl. No.: 277,802

[22] Filed: Nov. 30, 1988

[51] Int. Cl.$^5$ .............................................. C12N 9/24
[52] U.S. Cl. .................... 435/200; 435/209; 435/192; 435/190; 435/28; 435/886; 435/253.5; 435/277
[58] Field of Search ............... 435/200, 209, 192, 190, 435/28, 886, 253.5, 277

[56] References Cited

U.S. PATENT DOCUMENTS 4,089,745 5/1978 Antrim et al. ........................ 435/209
4,713,336 12/1987 Srinivasan et al. ................. 435/195

OTHER PUBLICATIONS

Tien and Kirk in *Science* (1983) 221:661–663.
D. Crawford in *Applied and Environmental Microbiology* (1978) 35:1041–1045.
Crawford, et al., *Applied and Environmental Microbiology* (1983) 45:898–904.
Mason et al., *Applied Microbiology and Biotechnology* (1988) 28:276–280.
Ramachandra, et al., *Applied and Environmental Microbiology* (1987) 53:2754–2760.
Tien et al., *Nature* (1987) 326:520–523.
Zhang, et al., *Biochemical and Biophysical Research Communications* (1986) 137:694–656.
Rafael Vicuna in *Enzyme Microb. Technol.* (1988) 10:646–655.
Tien, et al., *Proc. Natl. Acad. Sci. USA* (1984) 81:2280–2284.

Primary Examiner—Johnnie R. Brown
Assistant Examiner—Pamela S. Webber
Attorney, Agent, or Firm—Cooley Godward Castro Huddleson & Tatum

[57] ABSTRACT

A newly discovered lignin peroxidase enzyme is provided. The enzyme is obtained from a bacterial source and is capable of degrading the lignin portion of lignocellulose in the presence of hydrogen peroxide. The enzyme is extracellular, oxidative, inducible by lignin, larch wood xylan, or related substrates and capable of attacking certain lignin substructure chemical bonds that are not degradable by fungal lignin peroxidases.

16 Claims, 1 Drawing Sheet

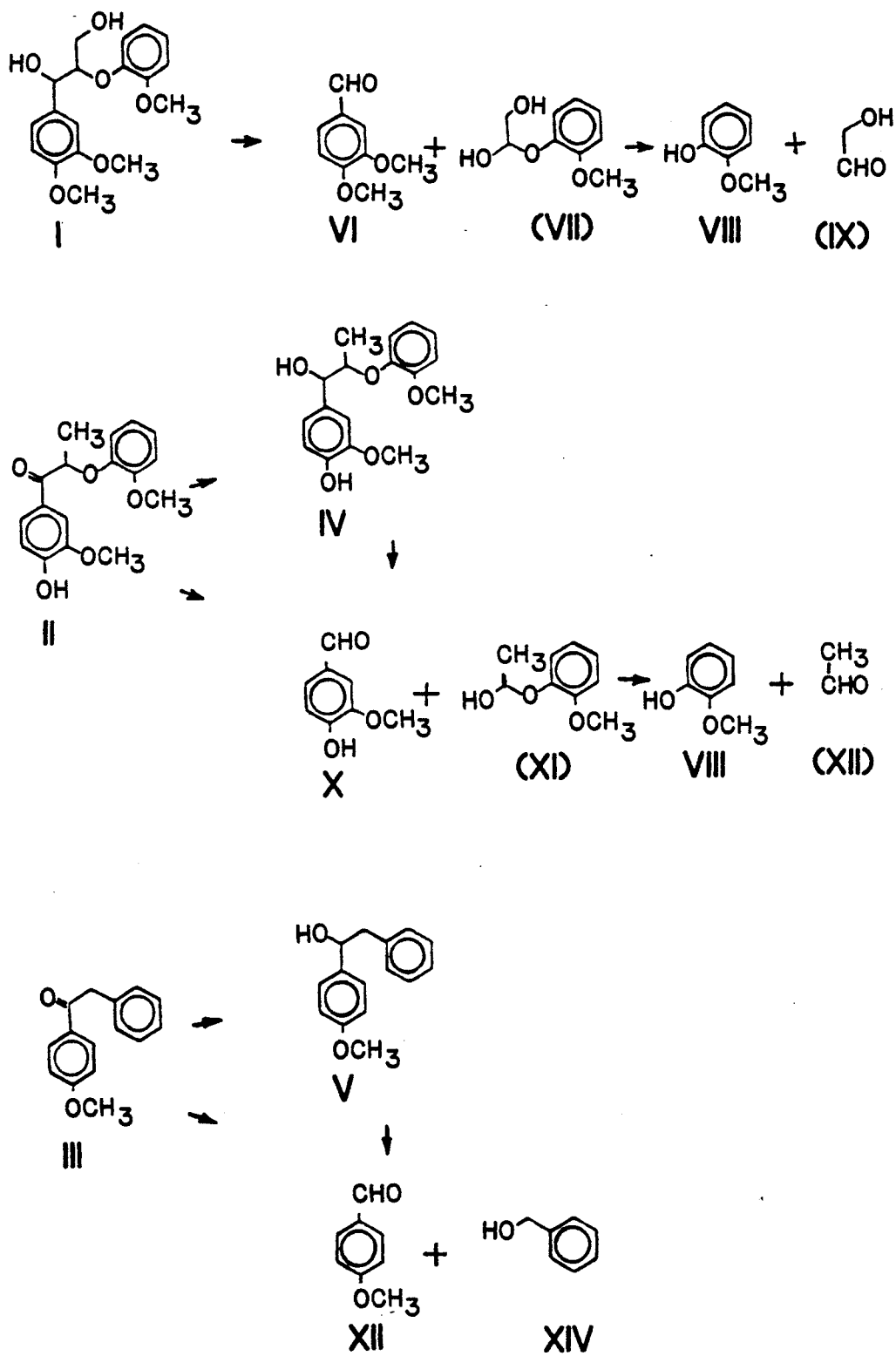

BACTERIAL EXTRACELLULAR LIGNIN PEROXIDASE

INTRODUCTION

1. Technical Field

The present invention is drawn to bacterial lignin peroxidase enzymes.

2. Background

Plant biomass, or lignocellulose, is, by far, the most important renewable resource and its bioconversion has immense ecological and potentially biotechnological importance. A major component of plant biomass, lignin, is regarded as the component which must be removed to allow efficient use of cellulosic material.

Lignocellulose is a complex of three primary polymers: lignin, cellulose, and hemicellulose. The plant cell wall is composed of cellulose microfibrils containing both highly crystalline and amorphous regions, embedded in a matrix oligocarbohydrate comprising polyphenolic lignin covalently bound to hemicellulose. Of these polymers, lignin is the most recalcitrant to degradation. Lignin comprises three types of aromatic monomers linked by a range of nonhydrolyzable bonds of which $\beta$-aryl-ether linkages are the most common. It is generally accepted that lignin degradation is the important rate-limiting step in lignocellulose biodegradation.

Lignin is a polymer of an aromatic alcohol of about 600–1000KD. It represents a class of substances that bind together cellulose fibers which make up a substantial portion of the woody portions of plant tissue. These heteropolymers are much harder, tougher, and more resistant to hydrolysis than cellulose. Of the interphenylpropane linkages which occur in the molecule, the $\beta$-0-4 type is the predominant linkage. In addition, there are other structural features which dictate constraints on the degradation of the molecule.

Lignin biodegradation is central to the earth's carbon cycle because lignin is second only to cellulose in abundance and, perhaps more significantly, because lignin physically protects most of the world's cellulose and hemicelluloses from enzymatic hydrolysis. Lignin is normally regarded as the component of lignocellulose which must be removed to allow efficient use of cellulosic material for saccharification, paper production or upgraded fodder. Biological delignification has the potential to provide an alternative to largely chemical processes which are energy-intensive, polluting and do not exploit utilization of lignin and its degradation products. Improving our understanding of lignin degradation by microorganisms would also have important implications for the prevention and treatment of wood decay and the biochemistry of soil humification.

Activity against lignin has been demonstrated in a relatively limited range of microorganisms. Perhaps the best studied, is the degradation of lignin in lignocellulose by white rot fungi *Phanerochaete chrysosporium*. Studies utilizing synthetic and natural substrates of the fungal system show that lignin biodegradation to $CO_2$ is a secondary metabolic activity, occurring during severe depletion of nitrogen or carbon sources. Some of the extracellular fungal enzymes involved in these reactions have been characterized.

There are problems associated with the use of fungal cultures in lignin degradation. First, fungi require particular culture conditions, such as humidity, aeration, temperature, and pH, which are not compatible with industrial processing environments. Secondly, fungi require long lag times and then, often, very slowly degrade lignin. Additionally, as fungi cannot grow solely on lignin, an additional food source must be added to support fungal growth.

The increasing interest in the exploitation of plant biomass as a renewable resource has provided an emphasis for research on microbial degradation of lignocellulose. Large quantities of wastes are currently being generated by forestry, agriculture and food processing which are not used for food, fuel or construction purposes. Much of this is either burned or allowed to decay naturally and can present problems such as air pollution or contamination of waterways.

To effectively exploit plant biomass as a renewable resource, alternative means of degradation of lignocellulose need to be explored.

RELEVANT LITERATURE

The purification of an extracellular lignin-degrading enzyme from *Phanerochaete chrysosporium* is reported by Tien, *Proc. Natl. Acad. of Sci. USA* (1984) 81:2280–2284 and Tien and Kirk *Science* (1983) 221:661–663. Streptomyces strains which carry out a limited attack on lignin were reported by D. L. Crawford, *Applied and Environmental Microbiology* (1978) 35:1041–1045. The isolation and characterization of a new intermediate form of a lignin degradation product by *Streptomyces viridosporus* was described by Crawford et al., *Applied Environmental Microbiology* (1983) 45:898–904. The use of protoplast fusion as a technique for genetically manipulating lignin-degrading Streptomyces strains is reported by Petty et al., *Applied Environmental Microbiology* (1987) 41:465–505.

The identification of extracellular proteins from actinomycetes which appear to be involved in the solubilization of lignocellulose is disclosed by Mason et al., *Applied Microbiological Biotechnology* (1988) 28:276–280 and Ramachandra et al., *Applied Environmental Microbiology* (1987) 53:2753–2760.

The identification of clones for a fungal ligninase gene is disclosed by Tien et al., *Nature* (1987) 326:520–523 and Zhang et al., *Biochemical and Biophysical Research Communications* (1986) 137:649–656.

Review articles on microbial degradation of lignin include Kirk et al., *Annual Review Microbiology* (1987) 41:465–505, A. G. McCarthy in *FEMS Microbiology Rev.* (1987) 46:145–163, and R. Vicuna *Enzyme and Microbiol Technology* (1988) 10:646–655.

SUMMARY OF THE INVENTION

A newly discovered lignin peroxidase enzyme is provided. The enzyme is obtained from a bacterial source and is capable of degrading both lignin and carbohydrate portions of lignocellulose in the presence of hydrogen peroxide. The enzyme is extracellular, oxidative, inducible by lignin, larch wood xylan, or related substrates and capable of attacking certain lignin substructure chemical bonds that are not degradable by known fungal lignin peroxidases. Isolation, characterization and uses of the enzyme are provided.

DETAILED DESCRIPTION OF THE INVENTION

In accordance with the present invention a newly discovered enzyme is provided which has been purified and has useful applications. The enzyme, a lignin peroxidase, has been isolated from a bacterial source and is found in higher than normal levels in bacterial strains enhanced for lignocellulose degradation. The enzyme, classified as a peroxidase, incorporates oxygen into cleavage products, requires hydrogen peroxide for activity, and is a major component of certain bacterial ligninolytic systems.

The present invention is concerned with bacterial lignin peroxidase enzymes. That is, enzymes which catalyze hydrogen peroxide-dependent oxidation of lignin and other various phenolic compounds. The enzymes show rapid hydrogen peroxide consumption when they are added to either milled corn lignin, or lignocellulose. The enzymes are heme proteins, exhibiting Soret bands in the visible range, 408 nm, and are inhibited by known heme inhibitors, such as potassium cyanide and sodium azide, at 1 mM concentration. Further, the absorption spectrum of the enzymes show distinct peaks at 280 nm and 408 nm, another characteristic of heme proteins.

The subject enzyme shows oxidative activity in a pH range of about pH 4.0 to about pH 8.0, preferably about pH 5.5 at a temperature of about 25° C. to about 50° C., preferably about 37° C. In general, moderately acidic pH conditions are optimal for lignin mineralization.

The lignin peroxidase enzyme is associated with primary growth of the bacteria. That is, it is presumed to be the result of primary metabolic activity and not dependent upon other factors such as stress to induce production. High concentrations of both organic and inorganic nitrogen in culture media do not inhibit lignin degradation by the enzyme.

The enzymes provided are capable of oxidation and depolymerization of native high molecular weight lignin using hydrogen peroxide as their oxidant. Although other lignin peroxidases have been described, such as in the fungus *Phanerochaete chrysosporium*, this is the first lignin peroxidase enzyme reported in a bacterium. The bacterial enzyme is capable of attacking certain lignin substructure chemical bonds that fungal lignin peroxidases cannot. It is capable of $C\alpha$-oxidation as well as $C\beta$-$C\beta$ cleavage of lignin and lignin substructure model compounds.

The instant enzyme is capable of digesting both $\beta$-0-4 and $\beta$1 type lignin substructure model compounds containing $C\alpha$-hydroxyl or $C\alpha$-carbonyl groups. Oxidative cleavage of $C\alpha$-$C\beta$ bonds of model compounds, 1,2-diarylpropane and arylglcerol-$\beta$-aryl ether types in the presence of hydrogen peroxide is observed. The enzyme preparation catalyzes $C\beta$-$C\beta$ bond cleavage in the side chains of the diaryl ethers, 1-(3,4-dimethoxyphenyl)-2-(2-methoxyphenoxy)propane-1,3-diol, 1-(4-hydroxy-3-methoxyphenyl)-2-(2-methoxyphenoxy)propan-1-one and a diaryl ethane, 1-(4-methoxyphenyl)-2-(phenyl)ethan-1-one.

This $C\beta$-$C\beta$ cleavage of $C\alpha$ carbonyl-containing compounds by the bacterial lignin peroxidase enzyme is in direct contrast to the action of lignin peroxidase of *P. chrysosporium*, which readily cleaved similar compounds only if they contain a hydroxyl group at the $C\alpha$ position. The $C\beta$- carbonyl group renders aromatic nuclei resistant to oxidation by the fungal lignin peroxidase. Therefore, the bacterial enzyme is more effective at lignin degradation than the fungal counterpart. This degradation of such $C\alpha$-carbonyl-containing compounds during bacterial-mediated lignin degradation is significant because the $C\alpha$-carbonyl content of the lignin increases during degradation by both Streptomyces and Thermomonospora spp.

One characteristic unique to the bacterial lignin peroxidase catalyzed degradation of lignin is the accumulation of acid-precipitable, polyphenolic, polymeric lignin (APPL) intermediates in the growth medium during lignin degradation in addition to the single ring aromatic phenols which are released. These unique degradation intermediates (APPLs) are water-soluable polymers consisting of a heterogenous mixture of molecular weight components of less than about 20 KD. The quantity of APPLs is correlated with the biodegradability of the lignocellulose type. Maximal recovery of APPL is obtained from corn lignocellulose, where recovery can reach as high as 30% of the initial lignin present in the substrate. Degraded APPLs are enriched in phenolic hydroxyl groups and, to a small extent, in carboxyl groups. Degradative products are largely oxidative and perhaps involve substantial cleavage of para-hydroxy ether linkages and methoxy groups in lignin.

The instant enzyme is associated with lignin-degrading bacteria. The enzyme is extracellular. When the bacteria is grown in culture, the enzyme occurs in the culture medium.

The lignin peroxidase enzyme is provided in a crude, partially pure, or purified form. Crude extracts of the enzyme may be prepared by growth of suitable bacteria in appropriate growth media. The cultures are grown until maximum levels of peroxidase activity are obtained. The actual time of growth of the cultures to obtain maximum levels of enzyme activity may vary. However, sample results based on shake flask experiments using 2,4-dichlorophenol as substrate show that maximum levels are generally obtained about 48 hrs. to about 96 hrs., usually about 72 hours. Maximum levels of enzyme are generally in the range of about 0.1 U/mg of protein to about 0.18 U/mg of protein, usually, about 0.14 U/mg of protein in medium without lignocellulose. For higher levels of peroxidase activity, the bacteria can be grown in the presence of lignocellulose. Peroxidase activity in the range of about 0.20 U/mg of protein to about 0.32 U/mg of protein, usually about 0.240 U/mg of protein, can be obtained when the bacteria are grown in medium supplemented with about 0.05% (w/vol) lignocellulose.

The addition of larch wood xylan to the bacterial culture in yeast extract-mineral salts medium enhanced extracellular 2,4-DCP peroxidase activity by 3-fold as compared to a medium without xylan, and 2-fold as compared to a medium supplemented with lignocellulose. By using a non-lignin inducer, it is possible to obtain a culture supernatant which does not contain APPL and other water-soluable, partially degraded lignin polymers. The use of a non-lignin inducer is significant as these intermediate polymers interfere with enzyme assays and complicate purification of the peroxidase enzyme.

The crude supernatant, that is, the growth medium containing larchwood xylan of a bacterial culture from which the bacteria and other cell debris have been separated, exhibits a specific activity of about 0.30 U/min/mg. However, the ligninase enzyme may be purified or partially purified by protocols employing conventional purification techniques known in the art, including ammonium sulphate precipitation, sepharose gel permeation chromatography and the like. Purification or partial purification of the lignin peroxidase results in an increase in specific activity of the enzyme. Thus, a specific activity of greater than 0.30 U/min/mg can be obtained upon partial purification. The purified enzyme preparation exhibits a specific activity of at least about 1.02 U/min/mg, resulting in at least a 34-fold increase in specific activity from the crude supernatant to the purified form of the enzyme.

The specific activities in the partially purified enzyme preparation, as determined by a spectrophotometric assay using 2,4-DCD and L-DOPA as substrate, are presented in Table 1. Additionally, both 2,4-DCP and L-DOPA oxidizing activities are inhibited with known peroxidase inhibitors such as potassium cyanide and sodium azide (Table 1).

The instant enzyme exhibits broad substrate specificity and is able to degrade lignin from a variety of sources including hardwood, softwood, and grass lignocellulose. The woody substrate may be in any form such as pulp, chips, or other processed or natural plant parts.

Bacterial sources of the ligninase enzyme include any bacteria that shows lignocellulose degradation activity, such as actinomycetes and in particular Streptomyces. Therefore, bacterial sources include but are not limited to Actinomycetales.

The actinomycetes include a heterogeneous group of gram-positive bacteria. The growth of most actinomycetes as branching hyphae is a trait shared by the filamentous fungi. A diversed range of actinomycete genera which exhibit differing ranges of degradative enzyme-mediated activities can be found in large numbers in soils, particularly forest or garden soils, and composts. Genera to which lignocellulose-degrading actinomycetes have been assigned include Streptomyces, Micromonospora, Microbispora, Thermomonospora, Actinomadura, Pseudonocardia, Saccharomonospora, Nocardia, and Rhodococcus.

The present invention encompasses bacterial lignin peroxidase enzymes in general. Now that a peroxidase enzyme has been reported from a bacterial source, any bacteria displaying lignin degrading activities can be screened for a lignin peroxidase enzyme. For example, isolation of bacterial sources of lignin peroxidase can be made by the protocol as set forth by Crawford et al. in *Appl. Environ. Mircrobiol.* (1978) 35:1041-1045, whose disclosure is incorporated herein by reference. In this procedure, isolations are made at room temperature from natural samples including forest soils, garden soils, and decomposing plant materials. In general, cultures are isolated by enrichment techniques, that is, by streaking and screening. Isolates are isolated after screening for the ability to cause substantial weight loss of lignocellulose. Procedures for the isolation of the enzymes from bacterial sources include those exemplified in the experimental sections as well as any enzyme isolation technique available in the literature.

As disclosed earlier, environments for the selection of bacteria with lignin-degrading activity include the soil, being a primary reservoir of degradative actinomycetes, and, in particular, composts. Another ecological niche where bacteria may be found having a role in lignocellulose degradation is as symbionts in the gut of higher termites.

Uses of the subject enzyme include both in vitro and in vivo applications. The major outlets for the products derived from lignocellulose degradation will be foods, feeds, fuels, chemicals and construction materials. The enzyme has a variety of potential uses including, but not limited to enzyme bleaching of pulp, aromatic assays for lignin content of plant tissue, upgrading lignocellulose wastes for animal fodder, composting of municipal solid waste and sewage sludge, specific oxidation of a broad range of aromatic compounds, depolymerization and specific chemical modification of lignin polymers, production of specialty chemicals from hydrolysis of lignin, food processing, decontamination of aromatic environmental pollutants, and the like. Further, the lignin intermediates, APPLs, provided by the bacterial enzyme may be prepared in high yield from waste lignocelluloses, such as corn stover, and have considerable potential as chemical feed stocks for a number of industries. Some potential industrial applications include the use of APPLs as surfactants or surfactant feed stocks and as polyurethane or adhesive precursors. Other potential applications which currently are not economic using fungal systems, include processes to produce glucose and/or ethanol directly or indirectly from lignocelluloses and the production of single cell protein for use as animal feed.

Other uses may involve modification of the ligninase enzyme, the ligninase gene, or the bacteria containing the enzyme. For example, with white rot fungi, mutants have been produced which lack cellulase. The action of these mutants is to degrade lignin and hemicellulose leaving the cellulose for pulp production. In the same manner, bacteria with modified enzyme systems can be produced for pulp production. Further, because of the ease of modification of bacterial genomes, especially compared to fungal systems, recombinant bacterial strains can be constructed for more efficient and rapid lignin degradation. With improved bacterial strains, biological delignification as an alternative to chemical pulping may be realized.

It will be beneficial to supply a continuous source of hydrogen peroxide to lignin degrading systems utilizing the instant bacterial lignin peroxidase enzyme. One means for supplying a continuous low concentration of hydrogen peroxide can be accomplished by including a carbohydrate source such as glucose, galactose, or the like, with an appropriate oxidase enzyme such as glucose oxidase, galactose oxidase, etc. into the lignin degrading system. In this manner, an efficient system for lignocellulose degradation would comprise sources of cellulase, oxidase and bacterial lignin peroxidase with an appropriate carbohydrate source.

The enzyme can be provided in any form including as an enzyme preparation or lysate. Enzyme preparation refers to any composition of matter that exhibits the desired enzyme activity and is derived from any useful microorganisms or compositions equivalent thereto. The term derived is used to refer to enzyme activity obtained from any source including whole microbial cells, dry cells, cell extracts and refined and concentrated preparations from cells and from culture supernatants.

Now that the enzyme has been identified and isolated, the gene for the lignin peroxidase can be identified and isolated by a number of ways. By partially sequencing the enzyme, DNA sequences that code for such partial peptides can be determined from a list of equivalent codons. Polynucleotide probes can then be prepared by synthetic chemistry and used in hybridization experiments to identify clones containing the gene. The gene can be isolated from a library such as a cDNA library or a chromosomal library. Once the clone(s) has been identified as annealing to the probe, the fragment containing the gene of interest may be isolated and manipulated.

Alternatively, a cDNA library may be constructed with mRNA isolated from lignin degrading bacterial cultures. By constructing the library in a suitable expression vector, such as λgt 11, recombinants containing the lignin peroxidase gene can readily be identified upon screening.

Alternatively, using a cDNA library, plaques of the cDNA clones can be screened with a polyclonal antibody raised against the ligninase enzyme. Phage DNA is then isolated from the positive clones and the cDNA insert size determined by agarose gel electrophoresis. Southern blot analysis can be used to confirm that the clones hybridized to an oligonucleotide probe synthesized from a sequence of amino acid residues of a ligninase enzyme. Sequencing of the cloned cDNA insert will give a complete sequence of the ligninase cDNA.

Once a complete gene has been identified, it may then be manipulated in a variety of ways to provide for expression. The entire gene with its native 5'- and 3' regulatory regions may be introduced into an appropriate expression vector. These vector systems have been developed with markers which allow for selection of transfectants as well as providing for convenient restriction sites into which the gene may be inserted. A wide variety of vectors exist which may be used for introduction by transformation, conjugation, transduction or transfection of the DNA sequence into a prokaryotic host.

Alternatively, a recombinant gene can be constructed which takes advantage of regulatory regions from other genes. This can be accomplished by constructing expression cassettes comprising the bacterial lignin peroxidase coding region flanked by foreign 5' and 3' regulatory regions, followed by insertion into an appropriate vector. Alternatively, the peroxidase gene can be inserted into expression vectors taking advantage of regulatory regions provided by the vectors. These vectors are constructed such that when the foreign gene is inserted at a convenient restriction site, a promoter is 5' to the inserted foreign gene which controls gene expression. In this manner, vectors which provide promoters that initiate transcription at high levels can be utilized for maximizing production of the peroxidase enzyme.

In general, expression may be enhanced by including multiple copies of the ligninase gene in a transformed host, by selecting a vector known to reproduce in the host producing large quantities of protein from exogenous inserted DNA, by using promoters which initiate transcription at high levels, or by any known means of enhancing peptide expression.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the area of genetic engineering.

In addition to the improvement of lignin degrading abilities of streptomycetes, the gene can be transferred into other bacteria for manipulation or expression. While the new bacterial host may not naturally excrete the enzyme, mechanisms to trigger the release of the enzyme, including cell death or chemical means, can be utilized.

Other means for the enhancement of the lignin degrading ability of bacterial strains include mutation and/or protoplast fusion of bacteria containing the ligninase gene. In particular, streptomyces strains enhanced for APPL production have been produced by ultraviolet irradiation mutagenesis and protoplast fusion. As the bacterial systems appear to be amenable to manipulation using these techniques, mutagenesis or protoplast fusion followed by screening for enzyme activity are available methods for strain improvement.

In general, strain improvement using recombinant techniques can be readily applied to bacterial systems, actinomycetes, particularly streptomycetes. A range of genetic manipulation strategies is available, based on the development of protoplast transformation and fusion techniques and the construction of plasmid and phage cloning vectors. Improving enzyme production by gene application and derepression, and the construction of recombinant strains which can selectively delignify or completely solubilize lignocellulose are important objectives. The application of recombinant DNA technology has great potential to overcome problems of insufficient yield. In the streptomycetes, in particular, hybrid antibiotic synthesis and the cloning of antibiotic biosynthesis genes have already been achieved, providing a background for the manipulation of other genetic systems.

The following examples are offered by way of illustration and not by way of limitation.

EXPERIMENTAL

Example 1

Enzyme Isolation and Characterization
Culture conditions.
Isolation and selection of lignocellulose-decomposing actinomycetes.

Isolations were made at room temperature from natural samples including forest soils, garden soils, and decomposing plant materials. Cultures were isolated by enrichment technique. Serially diluted natural samples were plated onto a mineral salts agar medium containing 40-mesh ground newsprint (0.5%) as a carbon and energy source and vitamin-free Casamino Acids (0.025%) as a supplemental nitrogen source. From original isolation plates incubated at room temperature, 30 mesophilic actinomycete strains were purified by restreaking onto the same medium. All of these isolates cleared newsprint agar to varying degrees within 7 to 14 days. Each isolate was screened for its ability to decompose lignocellulose in a 14-day growth experiment where the isolate was inoculated into 10 ml of lignocellulose medium in a test tube. The medium consisted of mineral salts solution containing 0.10% $KH_2PO_4$, 0.4% $Na_2HPO_4.7H_2O$, 0.02% NaCl, 0.02% $MgSO_4.7H_2O$, and 0.005% $CaCl_2.2H_2O$ plus 0.025% vitamin-free Casamino Acids (Difco) and a 0.5% level of ground, extracted fir lignocellulose. Lignocellulose and mineral salts plus Casamino Acids solutions were autoclaved separately, then mixed before inoculation. Inoculated cultures were incubated for 14 days at room temperature, under constant aeration. Sterile, humidified air entered each test tube through a glass-tube bubbler which penetrated nearly to the culture tube bottom. *S. viridosporus* T7A (ATCC 39115) stock cultures were maintained at 4° C. on yeast extract-malt extract-glucose agar. Spores from stock slants were inoculated into 2-liter flasks containing 1 liter of 0.6% (wt/vol) yeast extract (Difco Laboratories, Detroit, Mich.) in mineral salt solution plus 0.5% larchwood xylan (Sigma Chemical Co., St. Louis, Mo.) (YMX) and were grown for 3 days at 37° C. with shaking at 125 rpm.

After 3 days growth, culture supernatant solutions were harvested by filtering through glass wool. Proteins in the filtrate were concentrated 10-fold by ultrafiltration, and were then precipitated with ammonium sulfate (70% saturation). The precipitate was then resuspended in 20 mM 2-(N-morpholino)ethanesulfonic acid (MES) buffer (pH 5.5). Further purification was by gel filtration chromatography, using Sepharose CL-6B (Pharmacia Inc., Piscataway, N.J.) with MES buffer as eluent. Fractions exhibiting peroxidase activity were pooled and concentrated again by ultrafiltration.

Enzyme assay.

Peroxidase activity was routinely assayed with 2,4-dichlorophenol (2,4-DCP) (Sigma) as substrate. A final volume of 1.0 ml of reaction mixture contained 100 mM sodium succinate buffer (pH 5.5), 82 mM 4-aminoantipyrine (Sigma), 1.0 mM 2,4-dichlorophenol, 4.0 mM hydrogen peroxide and 100 μl of enzyme preparation. The reaction was initiated by the addition of hydrogen peroxide and the increase in $A_{510}$ was monitored for one minute at 37° C. One unit of enzyme was expressed as the amount of enzyme required for an increase of 1.0 absorbance unit per min.

Enzyme activity was also assayed using L-3,4-dihydroxyphenylalanine (L-DOPA; Sigma) as substrate.

Polyacryamide gel electrophoresis (PAGE) and peroxidase staining on gels.

Proteins in the enzyme preparation were analyzed by nondenaturing, discontinuous PAGE on a vertical slab gel (7.5% polyacrylamide). After electrophoresis, protein bands were visualized by Coomassie blue staining. Peroxidase bands were developed by activity staining with L-DOPA, 2,4-dichlorophenol, caffeic acid, homoprotocatechuic acid and N,N,N',N'-tetramethylphenylenediamine (TMPD) (all from Sigma) as substrates.

High Pressure Liquid Chromatography (HPLC) of proteins).

Proteins in the partially purified and crude enzyme preparations were analyzed on a Hewlett-Packard 1090A high pressure liquid chromatograph equipped with a HP-1040A diode array detector using a Pharmacia FPLC Mono Q anion exchange column. The mobile phase consisted of a gradient of 10 mM to 1M sodium acetate, pH 6.0, over a period of 40 min at a flow rate of 1 ml/min. The peaks were monitored at 280 and 409 nm and absorbance spectrum (250–600 nm) of each peak was recorded.

Example 2

Partial purification of peroxidase.

1000 ml of a 3-day YMX-grown culture supernatant fluid was concentrated 10-fold by ultrafiltration, and then subjected to ammonium sulfate precipitation (70% saturation). The precipitate was redissolved in 30 ml of 20 mM MES buffer (pH 6.0). This concentrated preparation was applied to a Sepharose CL-6B gel filtration column (1.5×100cm). Proteins were eluted from the column with 20 mM MES buffer (pH 6.0). The elution profile of the peroxidase from the gel filtration column exhibited the presence of four peroxidase isoforms. Only the major protein peak exhibited 2,4-DCP oxidizing activity. Fractions containing the major peak were pooled and concentrated again by ultrafiltration.

Four peroxidase isoforms from crude, concentrated supernatant fluids were observed when PAGE gels were stained for peroxidase activity with L-DOPA. Among the four isoforms, only the isoform designated P3 was also active against 2,4-DCP, homoprotocatechuic acid, caffeic acid and TMPD. Page gel activity staining with L-DOPA as substrate also showed only P3 in the partially purified preparation, as opposed to all four in the original culture fluid. The P3 band was also the major protein band when the gels were stained with Coomassie blue.

The purification steps described above yielded an enzyme preparation with a 36-fold increase in specific activity. The specific activities in the partially purified enzyme preparation, as determined by spectrophotometric assay using 2,4-DCP and L-DOPA as substrates, are presented in Table 1. Both 2,4-DCP and L-DOPA oxidizing activities were inhibited with known peroxidase inhibitors such as potassium cyanide and sodium azide (Table 1). Similar inhibition of activity was noticed during activity staining of PAGE gels.

Example 3

Enzyme Action on Model Compounds

Lignin substructure model compounds.

1-(3,4-Dimethoxyphenyl)-2-(2-methoxyphenoxy)propane-1,3-diol (I) was prepared by sodium borohydride reduction of 1-(3,4-dimethoxyphenyl)-3-hydroxy-2-(2-methoxyphenoxy) propan-1-one, which was synthesized as described by Landucci et al in *Holzforschung* (1981) 35:67-70. The model compounds 1-(4-methoxyphenyl)-2-(phenyl)ethan-1-one (III) and 1-(4-hydroxy-3-methoxphenyl)-2-(2-methoxyphenoxy)propan-1-one (II) made available by Dr. R. L. Crawford (Department of Bacteriology and Biochemistry, University of Id.).

Oxidations of lignin model compounds.

The model compounds were added to reaction mixtures at a final concentration of 0.02% (wt/vol). Reactions were carried out in a total volume of 3.0 ml, containing 0.1 mM hydrogen peroxide or a peroxide generating system consisting of 0.02 units/ml of glucose oxidase (Sigma) and 3 mM glucose 0.1M sodium tartrate buffer (pH 5.5) and 300 μl of enzyme preparation. Control reactions were performed with boiled enzyme preparation. Some reaction mixtures were flushed with oxygen and all were incubated at 37° C. for 18 hours on a shaker in slanting tubes. The reaction mixtures were then acidified to pH 2-3 with 12M HCl and extracted once with ether and once with ethyl acetate. Specific products were identified by gas-chromatography/mass-spectrometry (GC/MS) by comparing retention times with those of authentic standards, or by examination of their MS fragmentation patters alone where authentic standards were unavailable, or by HPLC.

Chromatographic analysis.

For GC, trimethylsilyl derivatives of extracted samples were prepared with 100 μl β-dioxane, 10 μl pyridine, and 50 μl N,O-bis(trimethylsilyl)acetamide. Each sample was held at 35° C. for 2 hours prior to injection. GC was performed on a Hewlett-Packard 5890 gas chromatograph with a flame ionization detector and an HP Ultra 2 capillary column (30mm×0.2mm) (Hewlett Packard Co., Santa Clara, Calif.). Column conditions were as follows. The oven temperature was 120° C. for 2 minutes followed by a 15° C. per minute gradient to 280° C., which was held for 15 minutes. The injector temperature was 240° C. and the detector temperature was 280° C. Mass spectral analysis was performed on a VG-7-7- HG mass spectrometer (VG International, U.K.) at 70 eV, which was coupled to the gas-chromatograph.

HPLC was performed on a Hewlett-Packard 1090A high pressure liquid chromatograph employing a HP-1040A diode array detector. During each run, chromatograms for 258, 280, and 310 nm were recorded and the ultraviolet (UV) absorbance spectrum (250-350 nm) of each peak was recorded at its front side, apex, and trailing side. A 100mm Hewlett-Packard microbore reverse phase column of Hypersil ODS with 5 μM particle diameter was used with a 40° C. column temperature, a 5 μl sampling loop, and a 0.4 ml/min flow rate. The gradient employed for solvent delivery was a mobile phase consisting of water adjusted to pH 3.2 with $H_2SO_4$ and acetonitrile. The percent of acetonitrile was 10% for 2 minutes, then increased to 50% over the next 10 minutes, and then increased to 100% over the following 5 minutes. The mobile phase was at 100% acetonitrile for the final 15 minutes; the total run time was 30 minutes. Products were identified by their specific retention times, and comparison of UV spectra with available standard compounds.

Peroxidase reaction with milled corn lignin (MCL) and lignocellulose.

The enzyme preparation (300 μl) was added to a reaction mixture of 3.0 ml containing 10 mg of either MCL (milled corn lignin), extracted corn-stover lignocellulose or cellulose (Whatman cellulose powder, W and R Balston Ltd., U.K.), 0.1M sodium succinate buffer (pH 5.5), and 1 mM hydrogen peroxide. The reaction mixtures were next incubated at 37° C., while hydrogen peroxide consumption was determined at regular intervals as described by Frew et al., Anal Chim Acta (1983) 155:139-150. At different time intervals, a known volume (100 μl) of the reaction mixture was added to 4-aminoantipyrine/phenol reagent and the $A_{505}$ of the resulting solution was measured. Hydrogen peroxide content was calculated from a standard curve.

Model compound oxidation.

FIG. 1 shows the lignin substructure model compounds which were oxidized by the partially purified peroxidase, and products that were formed. Only veratraldehyde, anisaldehyde and vanillin were detected by HPLC, GC, and GC/MS. Guaiacol, formed in trace amounts, was detected by HPLC, GC, and GC/MS. Small amounts of products (IV) and (V) were detected only by MS fragmentation. Minor peaks observed with oxidations of all three model compounds were suspected to be products derived from ring A. None of the above products were detected in the original substrate. The β-aryl ether dimer (I) was cleaved at the $C_\alpha-C_\beta$-bond to yield veratraldehyde (VI) and guaiacol (VIII). Vanillin (X) and guaiacol were formed from the diarylether (II), indicating similar $C_{6o}-C_\beta$ cleavage. The diarylethane (III) was cleaved between the $C_\alpha$ and $C_\beta$ carbons to yield p-anisaldehyde (XIII) as a major product. Mass spectra of model compound oxidation products are presented in Table 2.

Oxidations of the above lignin substructure model compounds occurred with or without flushing oxygen through the reaction mixture which was incubated on a shaker. Hydrogen peroxide was necessary for the reaction. Addition of hydrogen peroxide twice (once at time zero and once after 9 hr) during the incubation period, or generation of hydrogen peroxide by means of of the glucose-glucose oxidase system, yielded similar results. Enzyme activity was tested with acetate, tartrate, and succinate buffers, at pH 3.5 to 6.5. Among these buffers, sodium tartrate buffer (pH 5.5) was found superior for model compound oxidations, which did not occur above pH 5.5.

Oxidation of lignin.

The partially purified enzyme was incubated with extractive-free corn stover lignocellulose, MCL or pure cellulose under the same conditions used for enzyme assays. The rate of hydrogen peroxide consumption during reactions was monitored as an indirect measure of the oxidation of lignin structures (Table 3). Hydrogen peroxide was rapidly utilized when lignin substances (MCL and lignocellulose) were present in the reaction mixture, but not with cellulose powder or in the absence of substrate. Hydrogen peroxide was not consumed in control mixtures lacking enzyme or containing inactivated enzyme (boiled for 10 min).

Example 4

Purification of the Lignin Peroxidase

Growth Conditions.

Streptomyces viridosporus T7A was grown in a mineral salts-yeast extract (0.6% w/v) medium supplemented with 0.5% (w/v) larch wood xylan. Growth was aerobic with shaking at 37° C. Spores were used as the starting inoculum, and the incubation period was 48 hours.

Quantitative Lignin Peroxidase Assay.

The reaction mixture contained 0.16 mM 4-aminoantipyrine, 3 mM 2,4-dichlorophenol, 5.7 mM $H_2O_2$, and 200 μl of enzyme solution in a final volume of 1.0ml (buffered to pH 6.0). The reaction was initiated by addition of peroxide, and activity was followed by monitoring the change in optical density (O.D.) at 510 nm. One unit of activity was defined as the activity resulting in a change in O.D. of 1.0 absorbance unit under these assay conditions.

Lignin Peroxidase Purification and Molecular Weight Determination.

After 48 hours of growth, the streptomycete cells were removed from the medium by filtration. The enzyme-containing filtrate was then concentrated by Amicon membrane ultrafiltration using a PM10 Amicon filter. The lignin peroxidase in a 10-fold concentrated filtrate was precipitated by addition of ammonium sulphate to 70% saturation. The precipitate was resuspended in a small volume of 20 mM buffer of pH 6.0. Six ml of this enzyme preparation was loaded onto a Sepharose CL-6B 200 gel permeation column (bed volume, 150 cm) and chromatographed at a flow rate of 0.25 ml/min using the pH 6.0 buffer as eluant. Five ml fractions were collected. Lignin peroxidase activity in each fraction was assayed using the following reaction mixture; 2.85 mM 2,4-dichlorophenol, 0.23 mM 4-aminoantipyrine, 5.7 mM $H_2O_2$ in 100 μl of fraction. The assays were carried out in microtitre plate wells at 37° C. using a 5 minute incubation period. Active fractions turned brownish. The most active fraction, as determined by visual examination of the microtitre wells, was retained and assayed quantitatively for activity (see above), protein content (method of Lowry et al. *J. Biol. Chem.* (1951) 193:265-276), and specific activity (units/min/mg protein). To determine the molecular weight of the lignin peroxidase, molecular weight protein standards (Biorad kit) were subjected to SDS-PAGE gel electrophoresis, and a standard curve was prepared by plotting the log of the known molecular weight of each standard against its distance of migration on the gel. The lignin peroxidase was also subjected to electrophoresis, and its molecular weight was determined from the standard curve. Proteins were generally detected by staining with Coomassie blue. Biorad silver stain was for the determination of protein purity. The lignin peroxidase enzyme had a molecular weight of about 18 kD.

We have designated this new lignin oxidizing enzyme as actinomycete lignin peroxidase P3 (ALiP-P3).

The bacterial source and the enzyme itself offer advantages over the previously available fungal enzymes. The bacterial enzyme is expressed as a primary metabolite, is inducible by substances other than lignin, and it can attack certain lignin substructure chemical bonds that fungal lignin peroxidases cannot. The use of bacteria versus fungal systems offers other advantages, particularly in using actinomycetes. There is a strong background of expertise in large-scale cultivation of actinomyctes on a variety of substrates for commercial antibiotic production. Further, lignin degradation is subject to less stringent physiological ligninolytic activity than white-root rot fungi. As disclosed earlier, strain improvement using the recombinant DNA techniques can be readily applied to actinomycetes. In contrast, strain improvement by genetic manipulation is less attainable with fungi. Bacteria are more easily manipulated and it would be simple to genetically engineer bacterial strains that overproduce the enzyme, while this is a difficult task in fungi. In fungi, the gene must be transferred to a bacterium for genetic manipulation and expression. Even then, the genes are not always expressed in bacteria. Therefore, the use of the bacterial enzyme has the potential to overcome the problems of insufficient yield in ligninolytic systems.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

Inhibition[a] Of Peroxidase P3 Activities By Cyanide and Azide

| Treatment | Specific activity (Units/mg protein[b]) Substrate | |
|---|---|---|
| | 2,4,-DCP | L-DOPA |
| Control (no inhibitor) | 1.06 | 0.31 |
| With potassium cyanide | 0.45 (58%) | 0.15 (50%) |
| With sodium azide | 0.18 (83%) | 0.18 (41%) |

[a]Inhibitors were added at the final concentration of 1mM. Values indicate % inhibition.
[b]Protein content was determined by the Lowry method.

TABLE 2

Mass Spectra of Major Products Obtained From Oxidation of Lignin Model Compounds By Peroxidase.

| Product | Mass spectrum observed m/z (intensity in %) |
|---|---|
| Anisaldehyde (XIII) | 136(M+,10.0), 135(100), 107(10.3), 92(26.9), 77(34.2 |
| Benzyl alcohol (XIV) (as TMS derivative) | 180(M+,17.3), 165(35.4), 164(100), 149(16.6), 136(35.3), 135(15.2), 107(45.2), 91(67.3), 82(16.9), 77(17.2), 73(TMS+,69.1) |
| Guaiacol (VIII) | 196(M+,0.6), 180(0.3), 165(3.0), 149(1.5), 135(42.8), 91(6.2), 77(20.2), 73(TMS+,100) |
| Vanillin (X) (as TMS derivative) | 224(M+,10.1), 223(100), 209(4.4), 179(4.0), 165(8.4), 77(11.6), 73(TMS+,12.6) |
| Veratraldehyde (VI) | 166(M+,100), 165(40.4), 151(17.2), 135(22.1), 121(2.5), 95(52.4), 77(29.9) |

TABLE 3

Rate of Hydrogen Peroxide Consumption During Peroxidase P3 Reaction With Lignocellulosic Substrates.[a]

| Substrate | Hydrogen Peroxide Consumption (μmol/mg of enzyme/min) | |
|---|---|---|
| | With Enzyme | Without Enzyme |
| Lignocellulose | 1.51 | 0.09 |
| MCL | 0.75 | 0.09 |
| Cellulose | 0.76 | 0.09 |
| None | 0.40 | 0.09 |

What is claimed is:

1. A lignin peroxidase enzyme having a molecular weight of about 18 kD, enzyme activity that produces Cα-oxidation and Cα-Cβ cleavage of lignin and lignin degradation products, and a specific lignin peroxidase activity of greater than 0.30 enzyme U/mg.

2. The enzyme, according to claim 1, purified by at least one of ultrafiltration, ammonium sulphate precipitation, and Sepharose gel permeation chromatography.

3. The enzyme, according to claim 1, wherein said enzyme is inducible by lignin or larchwood xylan;

4. The enzyme, according to claim 1, wherein said enzyme is isolated from a member of Actinomycetales.

5. The enzyme, according to claim 4, wherein said member is from Streptomyces.

6. The enzyme, according to claim 5, wherein said member is from *Streptomyces viridosporus*.

7. A composition comprising a partially purified bacterial lignin peroxidase enzyme capable of degrading the lignin portion of lignocellulose in the presence of hydrogen peroxide and a carrier.

8. The composition, according to claim 7, wherein said enzyme has a molecular weight of about 18 KD, is inducible by lignin and larch wood xylan, and is capable of $C\alpha$-$C\beta$ cleavage of lignin and lignin degradation products.

9. The composition according to claim 7, wherein said composition exhibits, a specific lignin peroxidase activity of greater than 0.30 enzyme U/mg.

10. A method for the degradation of lignocellulose comprising contacting said lignocellulose with a bacterial enzyme preparation of lignin peroxidase in the presence of hydrogen peroxide for a sufficient time for said degradation.

11. A method, according to claim 10, wherein said lignin substrate is selected from hardwood, softwood, and grasses.

12. A method, according to claim 10, further comprising the addition of, glucose and glucose oxidase to provide said hydrogen peroxide.

13. A method, according to claim 12, further comprising the addition of cellulase.

14. Actinomycete lignin peroxidase P3.

15. The composition according to claim 7, wherein said composition exhibits a specific activity of greater than 1.0 enzyme U/mg.

16. The method of claim 10, wherein said lignin peroxidase has a molecular weight of about 18 kD, enzyme activity that produces $C\alpha$-oxidation and $C\alpha$-$C\beta$ cleavage of lignin and lignin degradation products, and a specific lignin peroxidase activity of greater than 0.30 enzyme U/mg.

* * * * *

UNITED STATES PATENT AND TRADEMARK OFFICE
CERTIFICATE OF CORRECTION

PATENT NO. : 5,200,338
DATED : April 6, 1993
INVENTOR(S) : Crawford et al

It is certified that error appears in the above-indentified patent and that said Letters Patent is hereby corrected as shown below:

Column 1, line 5, before INTRODUCTION, insert the following:

--The research was supported in part by the United States Environmental Protection Agency under Research Contract CR-815300-01-0, United States Department of Energy Grant DE-PG786ER13586, and National Science Foundation Grant VCS-8807000. The United States Government may have rights in this invention.--

Signed and Sealed this

Twenty-first Day of June, 1994

*Attest:*

BRUCE LEHMAN

*Attesting Officer*     *Commissioner of Patents and Trademarks*